(12) United States Patent
Sablone et al.

(10) Patent No.: US 12,016,762 B2
(45) Date of Patent: Jun. 25, 2024

(54) METHOD FOR ASSEMBLING KITS OF SANITARY PRODUCTS, AND RELATED APPARATUS

(71) Applicant: Fameccanica.Data S.p.A., San Giovanni Teatino (IT)

(72) Inventors: Gabriele Sablone, San Giovanni Teatino (IT); Massimiliano Rossetti, San Giovanni Teatino (IT)

(73) Assignee: Fameccanica.Data S.p.A.

( * ) Notice: Subject to any disclaimer, the term of this patent is extended or adjusted under 35 U.S.C. 154(b) by 0 days.

(21) Appl. No.: 17/959,385

(22) Filed: Oct. 4, 2022

(65) Prior Publication Data

US 2023/0104321 A1   Apr. 6, 2023

(30) Foreign Application Priority Data

Oct. 6, 2021   (EP) ..................... 21201297

(51) Int. Cl.
| | |
|---|---|
| *A61F 13/551* | (2006.01) |
| *A61F 13/15* | (2006.01) |
| *B65B 5/08* | (2006.01) |
| *B65B 35/02* | (2006.01) |
| *B65B 35/10* | (2006.01) |

(52) U.S. Cl.
CPC .. *A61F 13/55145* (2013.01); *A61F 13/15764* (2013.01); *B65B 5/08* (2013.01); *B65B 35/02* (2013.01); *B65B 35/10* (2013.01)

(58) Field of Classification Search
CPC .......... A61F 13/15764; A61F 13/55145; A61F 13/15747; B65B 5/08; B65B 5/108; B65B 5/06; B65B 5/106; B65B 35/10; B65B 35/44; B65B 35/04; B65B 35/02; B65B 35/40; B65B 35/54; B65B 2210/00; B65B 2230/02
See application file for complete search history.

(56) References Cited

U.S. PATENT DOCUMENTS

| | | | |
|---|---|---|---|
| 4,768,642 A | 9/1988 | Hunter | |
| 2013/0206640 A1* | 8/2013 | Mann, Jr. | ............... A47K 17/00 206/581 |
| 2013/0340390 A1* | 12/2013 | Carson | ............... G07F 17/0092 53/473 |

FOREIGN PATENT DOCUMENTS

| | | |
|---|---|---|
| EP | 0151034 A2 | 8/1985 |
| WO | 2021095954 A1 | 5/2021 |

OTHER PUBLICATIONS

European Search Report dated Mar. 18, 2022. 4 pages.

* cited by examiner

*Primary Examiner* — Thomas M Wittenschlaeger
(74) *Attorney, Agent, or Firm* — RMCK Law Group PLC

(57) ABSTRACT

A method and an apparatus are disclosed for assembling kits of sanitary products which involves loading of the sanitary products into containers including a plurality of independent housings for the sanitary products, each of the housings being configured to allow loading of a sanitary product therein and withdrawal of the sanitary product therefrom independently of the other housings.

14 Claims, 7 Drawing Sheets

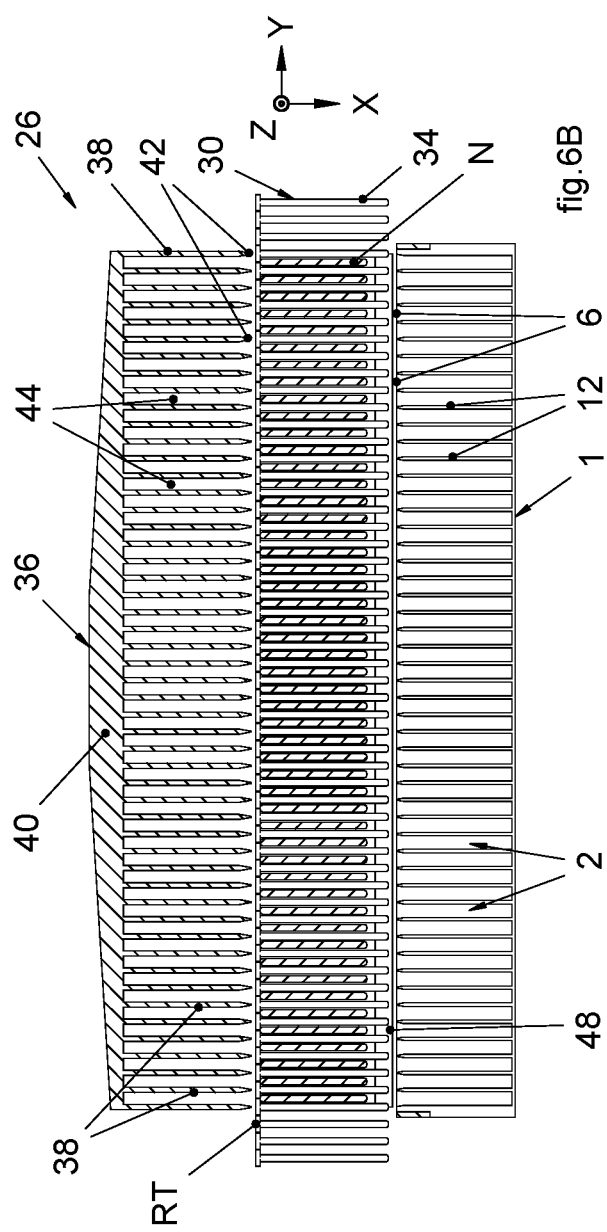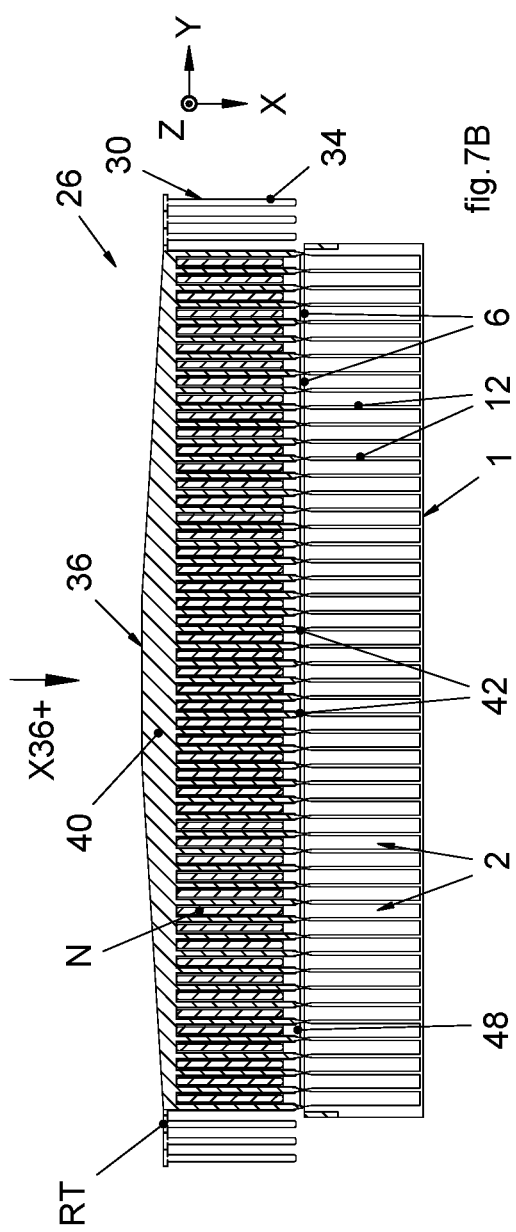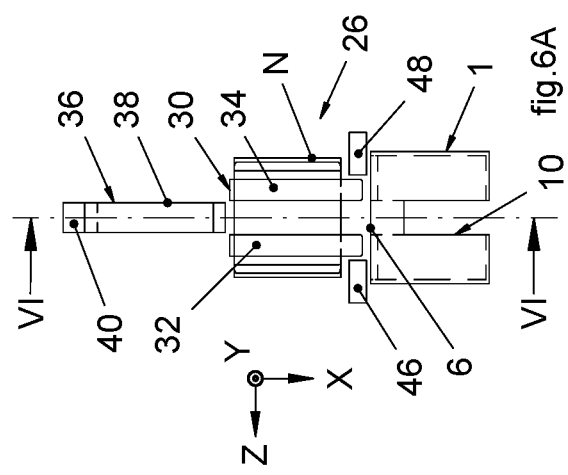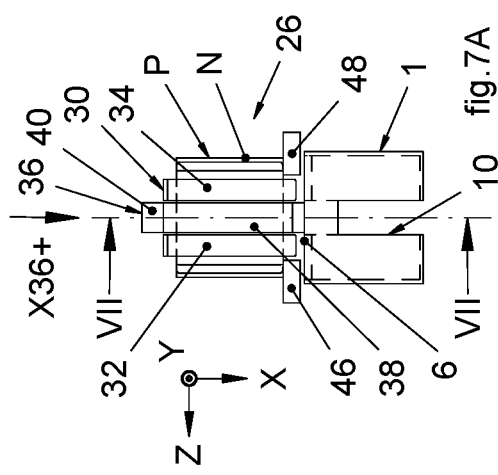

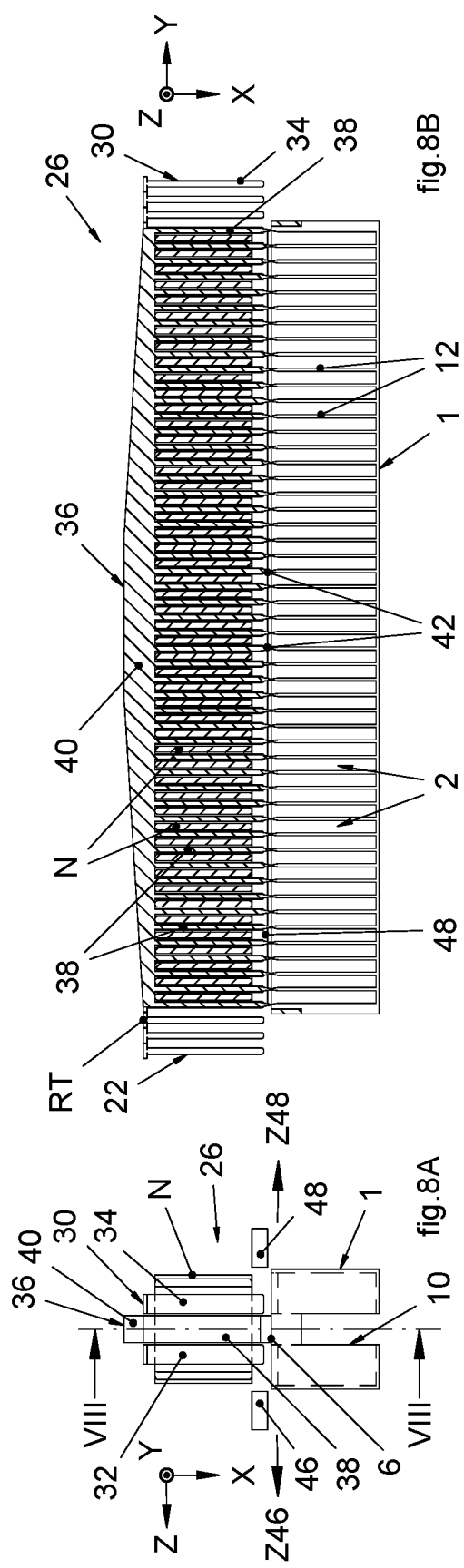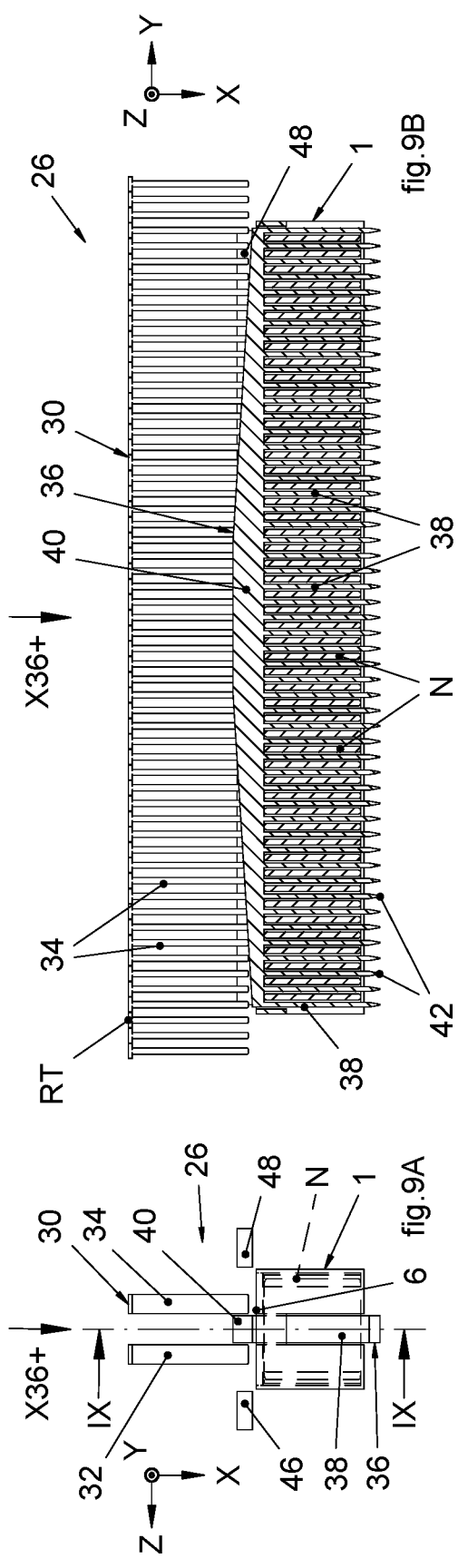

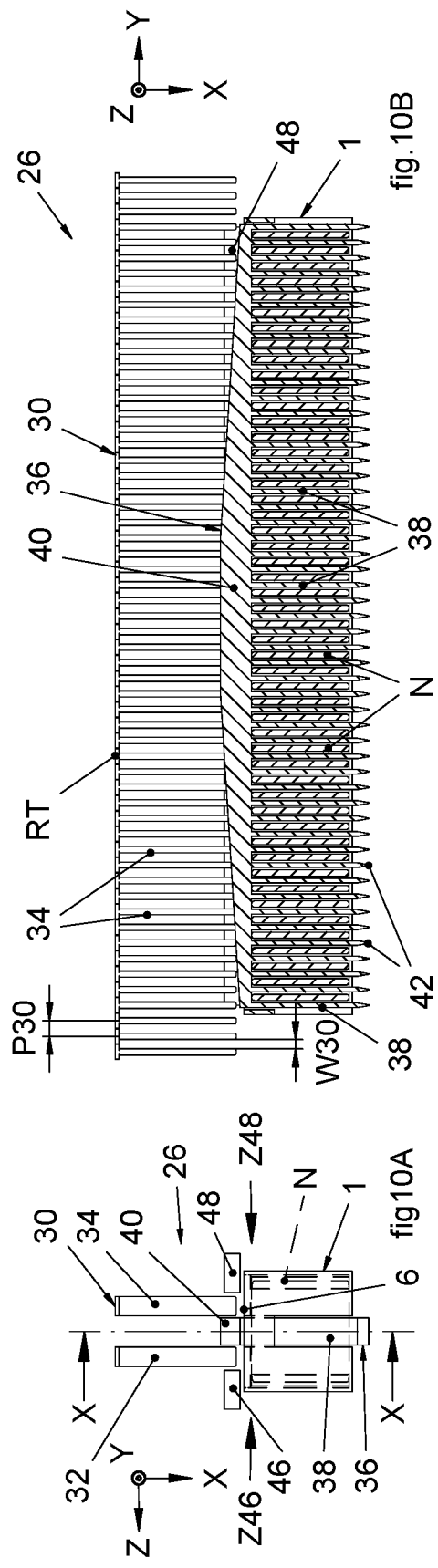
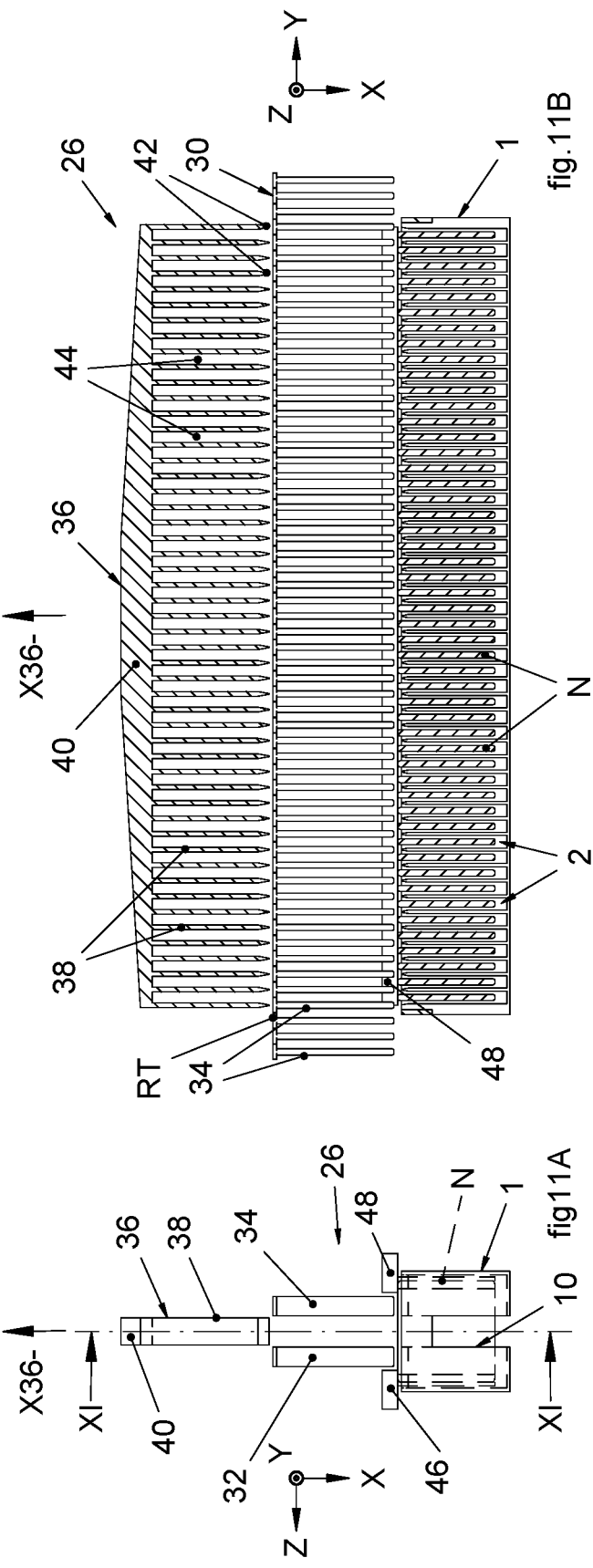

METHOD FOR ASSEMBLING KITS OF SANITARY PRODUCTS, AND RELATED APPARATUS

CROSS-REFERENCE TO RELATED APPLICATION

This application claims priority to European Patent Application No. 21201297.5 filed Oct. 6, 2021. The disclosure of the above application is incorporated herein by reference in its entirety.

FIELD OF THE INVENTION

The present invention relates to the packaging of sanitary products, particularly sanitary napkins.

PRIOR ART

Sanitary napkins are marketed all over the world in single format, single size packages. In other words, all of the sanitary napkins within the package are all identical and all have, accordingly, the same size and the same absorbent features.

The variability of the blood flow during a period calls for the use of different sanitary napkins throughout the period, starting from bigger and/or more absorbent products on the initial days, and transitioning to lighter or less absorbent products towards the final days. In view of the features of the packages of sanitary napkins, customers have no other option than buying multiple packages of different sanitary napkins, and picking the desired sanitary napkin from the corresponding package. This is clearly a drawback as the customer is forced to buy sanitary napkins way in excess of what would be actually needed to face the needs of the period.

An ideal condition would be that of having a mix of sanitary napkins configured to address the needs of different stages of the period all packaged together, so that the customer can buy a single packaged with napkins assembled as a "period kit", rather than a stack comprising one and the same product.

The technical problem underlying this derives from the manufacturing process that outputs the packaged sanitary napkins. Differently sized and/or differently performant sanitary napkins are usually manufactured by different machines operating in separate manufacturing and packaging lines. There is currently no possibility to merge different manufacturing lines together, with the result that the only possibility to assemble a "period kit", i.e. a package including a full range of sanitary napkins which address the needs of different stages of the period, consists in a manual assembly thereof, which is clearly unthinkable on an industrial scale.

OBJECT OF THE INVENTION

The object of the invention is to solve the above-mentioned technical problems. Particularly, the object of the invention is to provide a method and an apparatus for assembling, in an automated fashion, packages for sanitary napkins including a range of differently sized and/or differently performing sanitary napkins altogether making up a period kit.

SUMMARY OF THE INVENTION

The object of the invention is achieved by a method and an apparatus having the features forming the subject of the claims that follow, which form an integral part of the technical disclosure provided herein in relation to the invention.

BRIEF DESCRIPTION OF THE FIGURES

Further features and advantages of the invention will become apparent from the following description with reference to the annexed drawings, provided purely by way of non limiting example, wherein:

FIGS. 6A to 11B display an operating sequence of an apparatus according to the invention, with each feature/figure having an "A" portion and a "B" portion, each "A" portion being a side view and the corresponding B portion being a sectional view (according to respective sectional lines VI-VI, VII-VII, VIII-VIII, IX-IX, X-X, XI-XI) of portions A.

DETAILED DESCRIPTION

Figure 2:
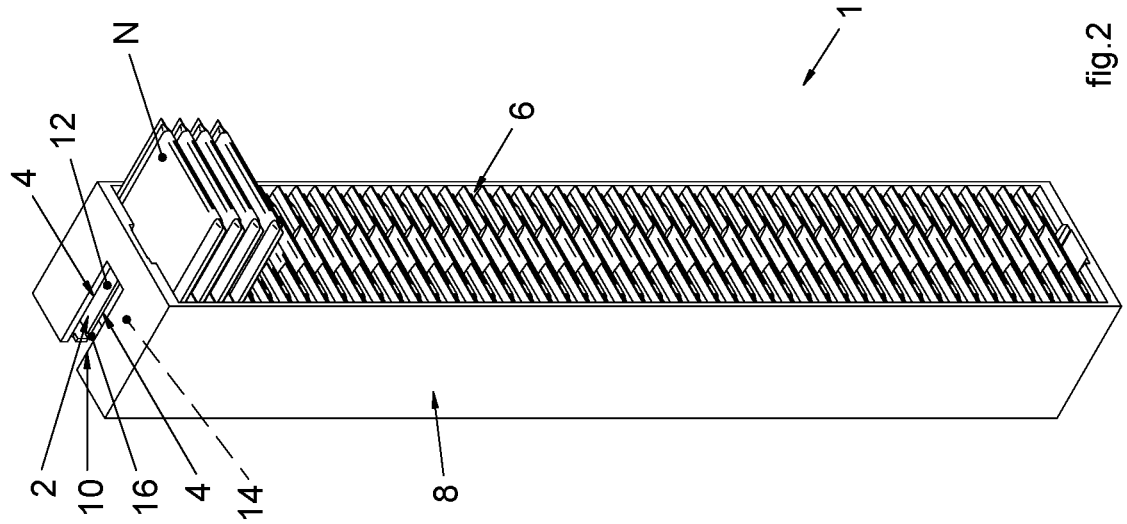
FIG. 2 is a perspective view according to pointer II in FIG. 1
Figure 1:
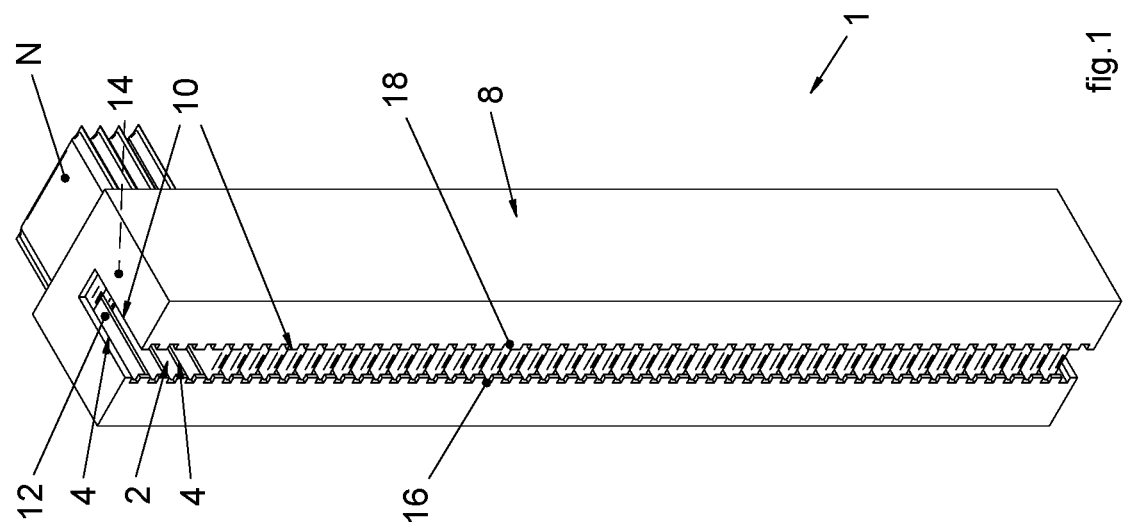
FIG. 1 is a perspective view of a component of an apparatus for carrying out the method of the invention.
Figure 3:
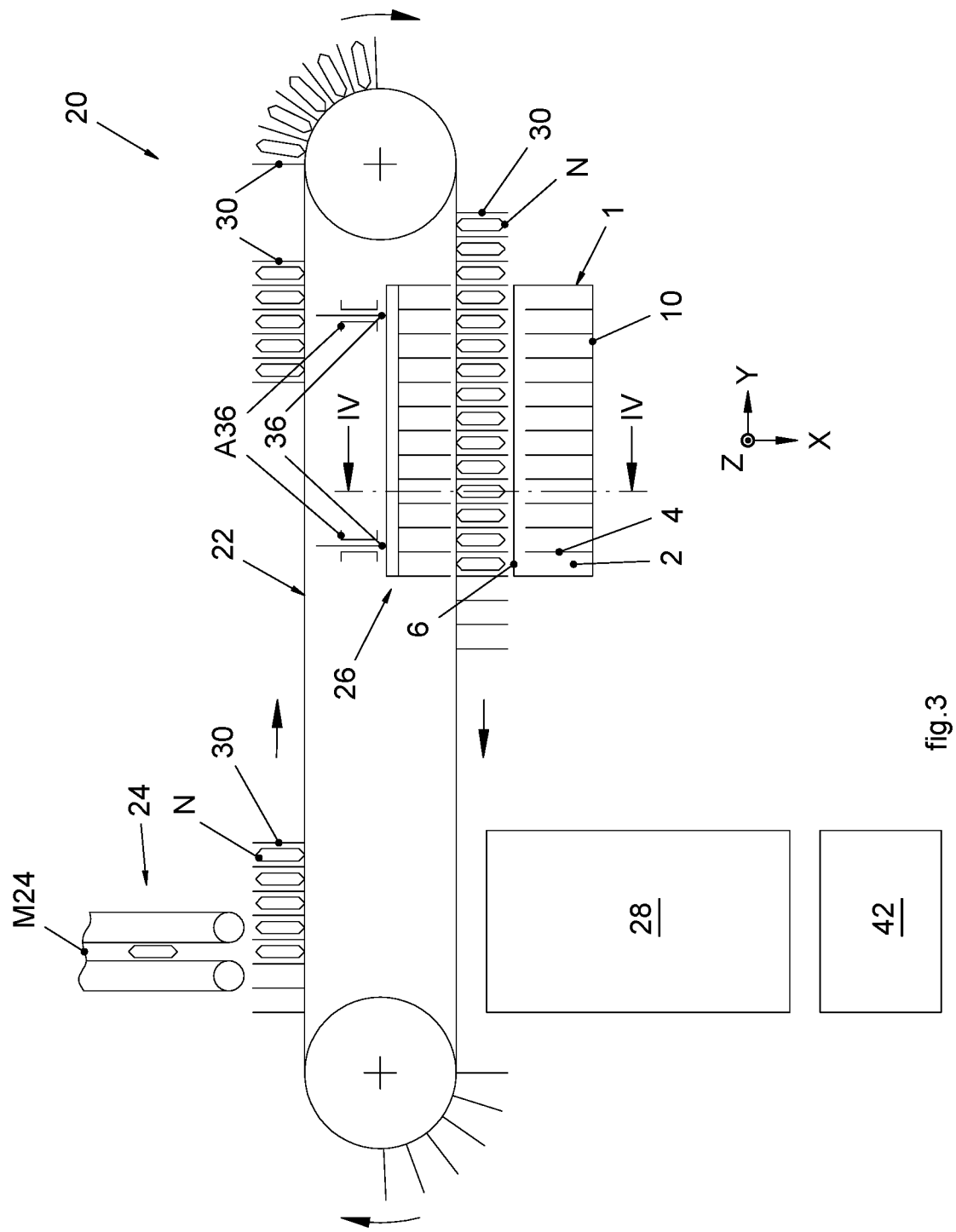
FIG. 3 is a schematic view of an apparatus according to the invention.
Figure 4:
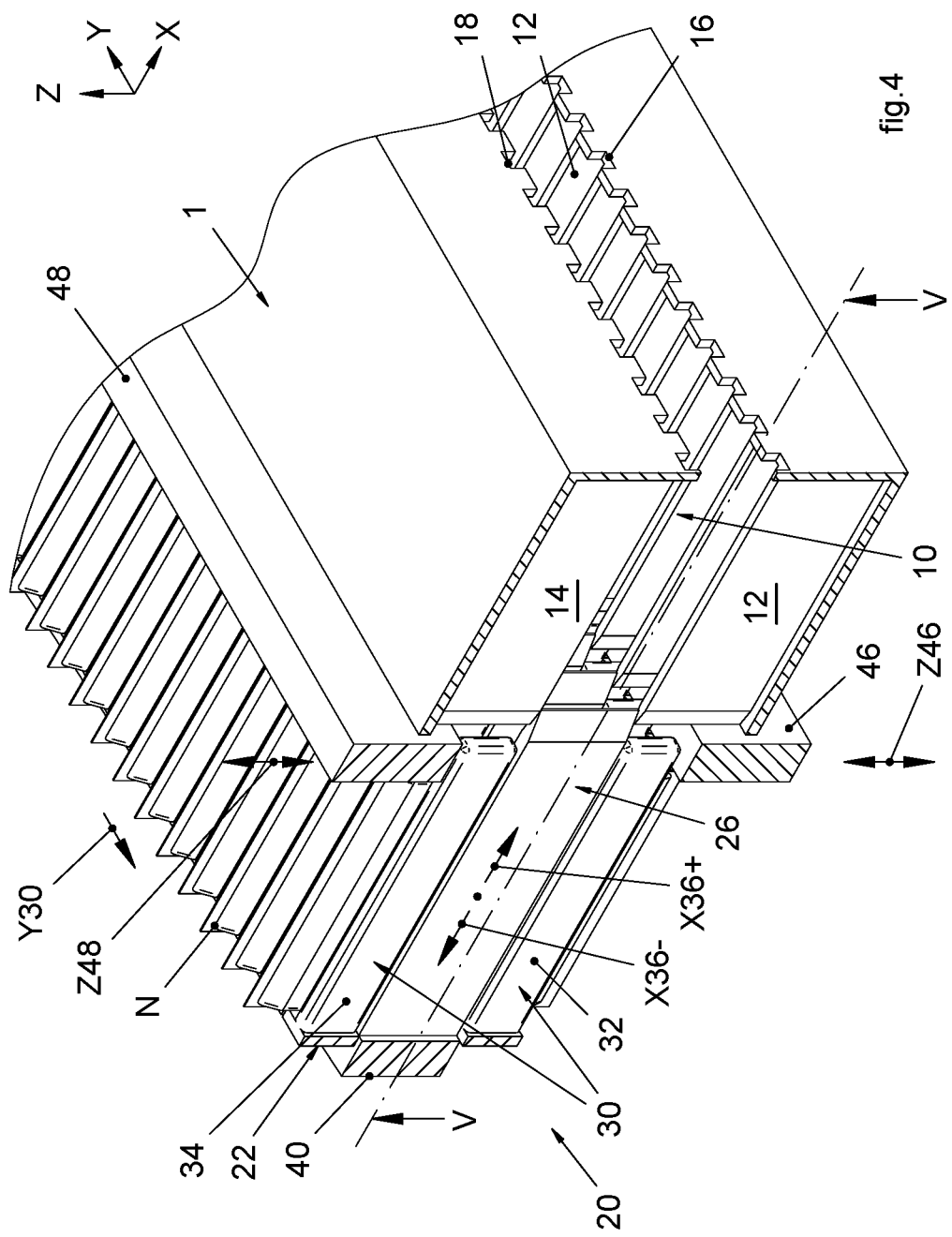
FIG. 4 is a schematic sectional view according to line IV-IV in FIG. 3.

Reference number 1 in FIGS. 1 to 3 designates as a whole a container that is part of an apparatus according to the invention, and also serves to carry out a method for assembling kits of sanitary products according to the invention. In preferred embodiments, each container 1 is a rack container comprising a rack of slot-like housings 2 separated by a baffle 4. Each of the housings 2 has an inlet opening 6, and all of the inlet openings 6 facing on one and the same side of the container 1. The housings 2 are fully independent from each other, i.e. each of the housing 6 is configured to allow loading of a sanitary product, particularly a sanitary napkin N, therein and withdrawal of the sanitary product therefrom independently of the other housings 2.

In the preferred embodiment shown in the figures, the container 1 has a container body 8 essentially prismatic (parallelepiped) in shape which is open to the outside where all of the inlet openings 6 give out, and which includes a cutaway 10 which extends across the rack of housings 2 and is arranged on an opposite side with respect to the inlet openings. Accordingly, each housing 2 comprises a first open end at the inlet opening 6, and a second open end at the cutaway 10, the second open end being opposite to the first open end.

Owing to the cutaway, each baffle 4 includes a first portion 12 and a second portion 14 arranged on opposite sides of the cutaway 10. Preferably, each baffle lies recesses with respect to the edge of the cutaway 10, i.e. it does not extend to the edge of the cutaway 10. In this regard, further cutaways 16, 18 may be advantageously provided at each pair of baffle portions 12, 14 respectively, so that the walls of the container body 8 arranged on opposite sides of the cutaway 10 have an overall comb-like shape due to the provision of the cutaways 16 and 18.

With reference to FIG. 3, reference number 20 designates as a whole an apparatus for assembling kits of sanitary products, particularly sanitary napkins N, according to the invention.

In various embodiments, the apparatus 1 comprises:
- one or more transfer conveyors 22 configured to receive a sanitary product output 24 from corresponding sanitary product manufacturing machines M24,
- a plurality of containers 1, each configured for loading with sanitary products N from one or more corresponding sanitary product outputs 24,
- a container loading unit 26 configured to retrieve sanitary products N from an associated transfer conveyor 22 and load it into corresponding housings 2 of a respective container 1, the container loading unit being arranged at a container loading location at least in part on an opposite side of the transfer conveyor 22 than a container 1 at the container loading location,
- a container handling facility configured for gathering the containers at a kit assembly location 28, and
- a withdrawal unit configured for collecting a sanitary products N from the containers 1 at the kit assembly location 28 and assembling the collected sanitary products into a kit.

Preferably, each transfer conveyor 22 is associated to one and a single sanitary product output 24, i.e. each machine M24 outputs the sanitary products N to one and a single transfer conveyor 22. Preferably, each of the machines M24 outputs a respective sanitary product—a sanitary napkin N—which is different from the sanitary products output from the other machines M24. It should be noted, however, that in other embodiments different groups of manufacturing machines may be configured to manufacture different products, whereby—for instance—three machines output a first type of sanitary product (for instance a sanitary napkin with high absorbent properties) and two machines output a second type of sanitary product (for instance a sanitary napkin for light blood flow). In such embodiments each machine may be associates to its respective transfer conveyor 22. Again, each conveyor will only receive products of the same type.

Regardless of the conveyor-machine association, the transfer conveyor 22 is configured for receiving the product output and handling the sanitary products to a container loading location whereat the sanitary products N are loaded into respective independent housings 6 of a container 1. The transfer conveyor 22 is preferably provided as a conventional closed loop conveyor.

The transfer conveyor 22 comprises a plurality of conveyor vanes 30, each configured to receive a sanitary product N at a dropoff location where the machine M24 outputs the sanitary products N (or in general where the product output of the machine M24 is conveyed). The conveyor vane also carries the sanitary product N through the conveyor 22 and to the container loading unit 26. The location of the loading unit 26 also determines the container loading location, as the loading unit 26 is configured to transfer the sanitary products N from the transfer conveyor 22 to the container 1.

Each conveyor vane 30 comprises a first portion 32 and a second portion 34 apart from the first portion 32. In other words, each conveyor vane 30 is essentially configured as a fork shaped conveyor vane.

With reference to FIGS. 3, 4, 5 and 6 through 11 (all sharing the same orthogonal reference system X-Y-Z), in preferred embodiments, the loading unit 26 comprises a transfer device 36 configured for engaging a batch of products P on the transfer conveyor 22 and transferring the batch to a container 1 standing by at a container loading station, wherein the container 1 remains stationary until loading of the batch of products P is complete. The transfer device 36 is configured as a comb having a plurality of teeth 38 protruding from a shaft 40. Teeth 38 are parallel to each other and preferably feature a tapered tip 42 to facilitate transfer operations.

The teeth 38 are preferably evenly spaced along the shaft 40, whereby a plurality of identical compartments 44 are defined between pairs of adjacent teeth 38. The compartments 44 each have a width W44 sized to receive a product P therein. The width W44 is preferably chosen to be substantially identical to the spacing between adjacent conveyor vanes 30 and adjacent baffles 4.

The loading unit 26 further comprises first and second abutment plates 46, 48, each movable and configured for operating a linear bidirectional motion along directions Z46 and Z48 so as to shuttle between a minimum mutual distance condition (visible for example in FIG. 4) and a maximum mutual distance condition. The abutment plates 48 are located between the vanes 30 and the container 1, and more specifically they are located at the open end of the vane 30, that which allows withdrawal of the product N therethrough. Accordingly, the abutment plates 46, 48—to the extent provided—are a part of the loading unit 26 that does not stand on an opposite side of the conveyor 22 than the container 1, as they actually stand on the very side of the container 1, facing the inlet openings 6.

In general the minimum and maximum mutual distance conditions correspond to species of first and second mutual distance conditions, the second mutual distance being higher than the first mutual distance, wherein in the first mutual distance condition an overlap is set up between each abutment plate 46, 48 and corresponding portions of the products N at the conveyor vanes 30, thereby preventing release of the products N from the vanes 30 (the way out is blocked), and wherein in the second mutual distance condition the above overlap is cancelled, thereby allowing release of the products N from the vanes 30.

As visible in greater detail in FIGS. 4, 5 and 6 through 11 the loading unit 26 is arranged so as to exhibit some degree of structural and functional interleaving with the conveyor 22 and the products N carried thereby. More in detail, the transfer device 36 is located at the transfer conveyor 22 and is positioned at an area in between the first and second portions 32, 34 of the conveyor vanes 30. The transfer device 36 is movable in a direction X36, suffixed by a "+" or a "−" depending on whether it is an outbound motion or an inbound motion, respectively (inbound and outbound are referred to the conveyor 22, whereby an outbound motion is representative of the transfer device 36 moving from the inside of the loop of the conveyor 22 out). The transfer device 36 is configured to operate between three positions (actuation is provided, for instance by one or more actuators A36, see FIG. 3), namely:
- a rest/standby position visible in FIG. 6 wherein the transfer device 36 is within the loop of the conveyor 22 and has no interaction with the products N on the conveyor vanes 30. In the rest position the loading unit 26 lies entirely on an opposite side of the conveyor 22 with respect to the container 1;
- a meshing position visible in FIGS. 5 and 7 (and—albeit in a different operating condition—FIG. 8), wherein the transfer device 36 is located in between portions 32, 34 of the conveyor vanes 30 and meshes with the products N
- a loading position visible in FIGS. 9 and 10, wherein the transfer device 36 is fully advanced into the container 1 and the loading of the products N into the housings 2 is complete.

Operation of the loading unit 26 will now be described. The following description applies regardless of the number and the shape of the products N, as well as regardless of whether the container 1 is fully loaded or not (in some embodiments, for instance, a container 1 may be partially loaded by a loading unit 26 transferring a first type of products N from a first transfer conveyor 22, and become fully loaded thanks to the transfer of a second type of products N from a second conveyor 22 by a second loading unit 26).

The loading unit 26 is arranged at least in part inside the loop of the conveyor 22 and on an opposite side of the conveyor 22 than the container 1 which stands by at the container loading location. In other words, the container 1 is arranged on the outside of the transfer conveyor 22 and in particular so that the inlet openings 6 face the conveyor vanes 30. The arrangement is better visible in FIGS. 4 and 5, as well as FIGS. 6 through 11.

Figure 5:
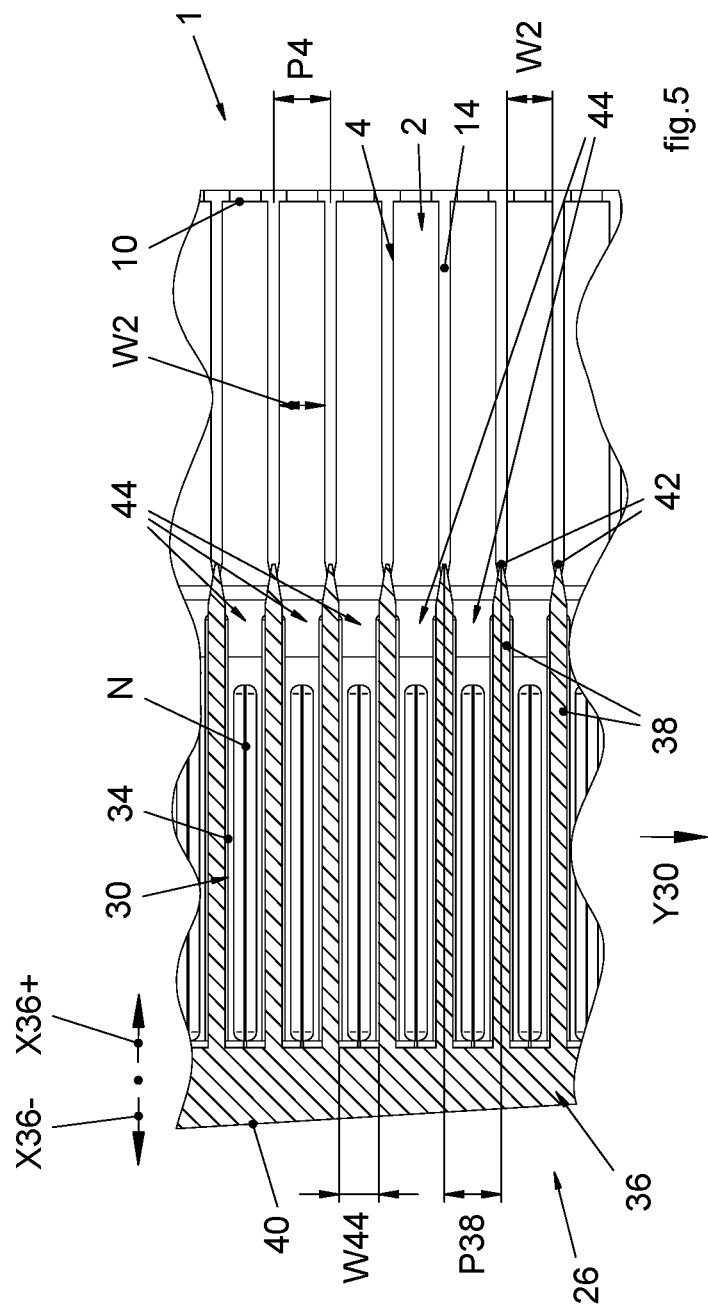
FIG. 5 is a perspective sectional view corresponding to FIG. 4.

As far as operation of the loading unit 26, the following is noted
- the teeth 38 of the transfer device 36 have a first pitch P38 (FIG. 5) and define the compartments 44 having a first compartment width W44 (FIG. 5),
- the vanes 30 of the transfer conveyor 22 have a second pitch P30 (FIG. 10) and define compartments having a second compartment width W30 (FIG. 10),
- the baffles 4 have a third pitch P4 (FIG. 5) and define said housings 2 having a housing width W2 (FIG. 5).

All of the pitches are referred to centrelines of the relevant items, as shown by the measurement takeoffs in the above-mentioned figures. The first pitch P30, the second pitch P38, and the third pitch P4 are substantially equal, and preferably the first compartment width W44 is substantially equal to said housing width W2 (the width W30 may vary due to the mounting of the vanes 30).

The loading of the container 1 begins under the conditions shown in FIG. 6: the loading unit is static, the transfer device 36 is in the standby position, and the conveyor 22 is stopped so as to line up each vane 30 with a corresponding tooth 38 (of course "each vane 30" is meant as far as the extension of the transfer device 36 in the direction Y). Better put, alignment is such that each tooth 38 comes to be aligned with a root RT of a corresponding vane 30, provided that the remainder of the vane is not bound to a specific orientation as it has the possibility to tilt, pivoting at the root RT, to accommodate bends in the path of the conveyor 22. The root RT is the location at which the pitch P30 is defined.

The abutment plates are in the condition of first (minimum in this case) mutual distance, which obstructs the way out of the products N from the vanes 30, whereby the latter cannot accidentally escape therefrom. In some embodiments, the abutment plates may possibly be kept at a mutual distance that is above the minimum one so as not to hinder the way out for the products N, but this option generally comes at the price of controlling an immediate closing up of the abutment plates, as the subsequent operating condition of FIG. 7 requires them to block the way out for the products N.

Next, FIG. 7, the transfer device 36 is moved into engagement (motion X36+, meshing position is reached) with the products N, and overall the comb shape thereof literally meshes with the products N still located between the vanes 30. Meshing comprises gradual enclosure of the products N by the compartments 44. Advancement is made possible thanks to the split arrangement of the vanes 30, which—as best visible in FIG. 4—accommodate the teeth 38 between portions 32 and 34.

Advancement of the transfer device 36 extends at least as far as required for reaching double contact at opposite ends of the products N, i.e. a first contact with the shaft 40 at a first end of the products N, and a second contact on the abutment plates 46, 48 at a second (opposite) end of the products N. The transfer device 36, together with the abutment plates 46, 48, operates to reset the orientation and the alignment of the products N prior to loading the same into the container 1. In other words, loading involves sliding the products N each into a corresponding, well delimited, housing 2, and this requires the products N to be fully aligned with the housings as well as oriented according to the sliding direction. Here, the combination of the comb shaped transfer device 36 and the abutment plates 46, 48 provides the reset just by advancement of the transfer device 36. The orientation and the alignment of the products N may in fact be far from optimal when the conveyor 22 is stopped at the loading unit 26, essentially in that, as anticipated, the vanes 30—which are mounted onto a driving chain—are freely oscillating relative to the chain due to the need for accommodating bends in the conveyor path. When stopped at the loading unit 26, the vanes of the conveyor 22 are randomly oriented, i.e. they may be tilted forwards or backwards with respect to a direction of motion of the conveyor 22 (Y22 in FIG. 4) so that alignment thereof with the baffles 4 is not reached.

The insertion of the transfer device 36 between blade portions 32 and 34 actually provides a "straightening" action on the products N: the latter are forced to orient according to the teeth 38 as the products N gradually become enclosed by the compartments 44 also straightening the orientation of the blades 30, so that each product N becomes fully aligned with the sliding direction of insertion into the housings 2. Not only this: while advancing the transfer device 36 in between the blades, the batch of products N is forced to advance towards the abutment plates until the double contact referred to above is reached. The double contact also restores alignment between the products N, whereby they come out of the operations represented in FIG. 7 straightened up and aligned with the housings 2, as well as fully aligned with each other.

Further on, FIG. 8, the abutment plates 46, 48 are moved towards the condition of second (maximum in this case) mutual distance. This clears the way for the products N to leave the vanes 30 (better put, the vane compartments). This condition may not be reached immediately, but it generally reached (FIG. 9) together with the further advancement (X36+ again, the loading position of the transfer device is reached) of the transfer device 36 into the container 1, which slides the products N off the vanes 30 and into the housings 2, which are lined up with the compartments 44.

In this condition, the teeth 38 are located in the cutaway 10 between the portions 12 and 14 of the baffle 4, and preferably protrude out of the back of the container 1, through cutaways 16, 18. The tapered tips 42 help in preventing jamming of the transfer device 36 when the latter is introduced into the container 1 starting from the condition of FIG. 6.

Next, FIG. 10, the abutment plates are brought back to the first (minimum) distance condition while the transfer device 36 is still into the container 1 meshed with the products N, and the transfer device 36 is ready to be retrieved (FIG. 11), i.e. retracted from the container 1—motion X36− towards the rest/standby position, which leaves the products N into the housings 2 as the teeth 38 are not configured to provide any drawings action of the products N in the direction X36−. Again, the tapered tips 42 make sure that no shoulder or abutment is created that could possibly draw the freshly loaded products N out of the container 1. The loading cycle then restarts again from the condition of FIG. 6. In some embodiments, the abutment plates 46, 48 may be dispensed with, thereby relying on the sole "straightening" action of the teeth 38 in the meshing position and achieving full alignment of the products N only when a double contact is established that involves a first contact between a first end of the products N and the shaft 40, and a second contact at a second (opposite) end of the products N and the container walls on opposite sides of the cutaway 10.

As already noted, the transfer device 36 may be only partly filled with products N, thereby loading a portion of the container 1. Fill-up may be achieved by another partial loading at another loading unit 26 to populate the housings that remained vacant following the first loading.

Once a container 1 is fully loaded with a batch of sanitary products N, the container 1 is transferred to the kit assembling area 28 by a handling facility. The handling facility may comprise, for instance, automated guided vehicles (AGV) or overhead transfer units capable of picking and releasing the container 1 at the area 28. The area 28 hosts several containers 1, each loaded according to the method disclosed above. Because the containers 1 were loaded with the product output from different machines, the area 28 gathers plural batches of different sanitary products N which may be individually collected from the containers 1—thanks to the independency of the housings 6—and assembled into a kit. If the product N is a sanitary napkin, the different sanitary napkins may be individually collected from the respective containers and assembled into a period kit. Collection of the sanitary products by retrieval from the containers 1 is preferably performed by means of a picking robot. The picking robot is also preferably used to assemble the very kit.

Conveniently, a packaging machine 42 is provided at the kit assembling area 28 whereby once the kits are assembled, they can readily be packaged and sent on to further processing or logistics stages.

Thanks to the invention, it is possible to assemble virtually whatever kit of sanitary products, regardless of the fact that the products in the kit are manufactured by different machines not operatively connected or interconnected to each other. While the description herein has been provided with primary reference to a kit of sanitary napkins, any sanitary product can be processed according to the method and by the apparatus of the invention.

Naturally, while the principle of the invention remains the same, the details of construction and the embodiments may widely vary with respect to what has been described and illustrated purely by way of example, without departing from the scope of the present invention.

The invention claimed is:

1. A method for assembling kits of sanitary products, comprising:
receiving a sanitary product output from a plurality of manufacturing machines thereof,
transferring the sanitary products in the sanitary product output from each manufacturing machine of the plurality of manufacturing machines into a respective container, each container including a plurality of independent housings for the sanitary products, each of the plurality of housings being configured to allow loading of a sanitary product therein and withdrawal of the sanitary product therefrom independently of the other housings of the plurality of housings, and
collecting sanitary products from the plurality of housings of said containers and assembling a kit of sanitary products comprising a plurality of sanitary products from different containers,
wherein said transferring the sanitary products comprises receiving the sanitary product output from the plurality of manufacturing machines onto a transfer conveyor at a drop off location, and handling the sanitary products to a container loading location whereat the sanitary products are loaded into respective housings of the plurality of housings.

2. The method of claim 1, wherein the transfer conveyor comprises a plurality of conveyor vanes, each sanitary product being dropped off at a respective conveyor vane of the plurality of conveyor vanes.

3. The method of claim 2, wherein each container is a rack container comprising a rack of housings, each of said housings being separated by a baffle, wherein each baffle includes a first portion and a second portion arranged on opposite sides of a cutaway, the cutaway extending across the rack of housings, wherein each of the housings has an inlet opening, all of the inlet openings facing on one and the same side of the container, and wherein the cutaway is arranged on an opposite side to the inlet openings.

4. The method of claim 3, wherein the plurality of conveyor vanes each comprise a first portion and a second portion apart from the first portion.

5. The method of claim 4, wherein transferring the sanitary products in the sanitary product output from each manufacturing machine into the respective container comprises:
providing a container loading unit at the transfer conveyor on an opposite side of the transfer conveyor than the respective container, the container loading unit comprising a transfer device, the transfer device being comb shaped and including a plurality of teeth protruding from a shaft and defining compartments therebetween,
stopping the transfer conveyor at the container loading unit so that each tooth of the plurality of teeth of the transfer device is aligned with a root of a vane of the plurality of vanes of the transfer conveyor, whereby each compartment between adjacent teeth is also aligned with a corresponding housing of the respective container,
advancing the transfer device into the vanes, thereby bringing the teeth in between the first portion and the second portion thereof, and enclosing the sanitary products into the respective compartments of the transfer device,
further advancing the transfer device into the respective container, thereby bringing the teeth between the first portion and the second portion of the baffles, and sliding the sanitary products into the respective housings,
retracting the transfer device from the respective container.

6. The method of claim 5, wherein said container loading unit further comprises first and second abutment plates arranged on opposite sides of the transfer device, and also arranged on opposite sides of the plurality of conveyor vanes, the first and second abutment plates being movable to vary a mutual distance therebetween,
wherein the method further comprises:
positioning the first and second abutment plates at a first mutual distance to set up an overlap between each abutment plate and corresponding portions of the sanitary products at the plurality of conveyor vanes prior to advancing the transfer device into the plurality of conveyor vanes, advancing the transfer device into the plurality of conveyor vanes until a double contact is reached between the shaft and a first end of the products and the first and second abutment plates and a second end of the sanitary products, positioning the first and second abutment plates at a second mutual distance, higher than the first mutual distance, to cancel the overlap between each abutment plate and corresponding portions of the sanitary products at the plurality of conveyor vanes prior to advancing the transfer device into the plurality of conveyor vanes, further advancing the transfer device into the respective container.

7. The method of claim 6, wherein said first distance is a minimum mutual distance, and said second distance is a maximum mutual distance.

8. The method of claim 1, wherein loading of the sanitary product into the respective housing comprises positioning the sanitary product at the respective housing, and sliding the sanitary product into the respective housing.

9. The method of claim 1, wherein said collecting sanitary products from the plurality of housings of said containers and assembling the kit of sanitary products comprises gathering the containers at a kit assembling area and withdrawing the sanitary products from the plurality of housings of the containers at the kit assembling area to assemble the kit of sanitary products.

10. The method of claim 9, wherein said withdrawing the sanitary products from the plurality of housings comprises picking the sanitary products by means of a robot, and further assembling the kit of sanitary products by the robot.

11. An apparatus for assembling kits of sanitary products, the apparatus comprising:
one or more transfer conveyors configured to receive a sanitary product output from a corresponding sanitary product manufacturing machine,
a plurality of containers, each container configured to be loaded with sanitary products from one or more sanitary product outputs, and each container including a plurality of independent housings for the sanitary products, each of the plurality of housings being configured to allow loading of a sanitary product therein and withdrawal of the sanitary product therefrom independently of the other housings of the plurality of housings,
a container loading unit configured to retrieve sanitary products from a transfer conveyor and load the sanitary products into corresponding housings of the plurality of housings of a respective container of the plurality of containers, the container loading unit being arranged at a container loading location at least in part on an opposite side of the transfer conveyor than the respective container at the container loading location,
a container handling facility configured for gathering the plurality of containers at a kit assembly location,
a withdrawal unit configured for collecting a sanitary products from the plurality of containers at the kit assembly location and assembling the collected sanitary products into a kit of sanitary products.

12. The apparatus of claim 11, wherein:
each container is a rack container comprising a rack of housings, each of said housings being separated by a baffle, wherein each of the housings has an inlet opening, all of the inlet openings facing on one and the same side of the container, and further wherein each baffle includes a first portion and a second portion arranged on opposite sides of a cutaway, the cutaway extending across the rack of housings and being arranged on an opposite side to the inlet openings,
the transfer conveyor comprises a plurality of the conveyor vanes, each configured to receive a sanitary product, each conveyor vane of the plurality of conveyor vanes comprising a first portion and a second portion apart from the first portion,
the container loading unit comprises a transfer device, the transfer device being comb shaped and including a plurality of teeth protruding from a shaft and defining compartments therebetween,
and further wherein the transfer device is configured to operate between three operating positions including:
a standby position wherein the transfer device is on an opposite side of the transfer conveyor with respect to the respective container;
a meshing position wherein the transfer device is located in between the first and second portions of the conveyor vanes and meshes with the sanitary products so that the compartments enclose corresponding ones of said sanitary products,
a loading position wherein the transfer device is advanced into the respective container and the sanitary products are loaded into the corresponding housings.

13. The apparatus of claim 12, wherein said loading unit further comprises first and second abutment plates arranged on opposite sides of the transfer device, and also arranged on opposite sides of the plurality of conveyor vanes and at a position comprised between the plurality of conveyor vanes and the respective container, the abutment plates being movable to vary a mutual distance thereof between:
a first mutual distance configured to set up an overlap between each abutment plate and corresponding portions of the sanitary products at the plurality of conveyor vanes,
a second mutual distance, higher than the first mutual distance, that cancels the overlap between each abutment plate and corresponding portions of the sanitary products at the plurality of conveyor vanes.

14. The apparatus of any of claim 12, wherein:
the plurality of teeth of the transfer device have a first pitch and define compartments having a first compartment width,
the plurality of vanes of the transfer conveyor have a second pitch and define compartments having a second compartment width,
the baffles have a third pitch and define said plurality of housings each having a housing width,
wherein said first pitch, said second pitch and said third pitch are substantially equal, and wherein the first compartment width is substantially equal to said housing width.

* * * * *

UNITED STATES PATENT AND TRADEMARK OFFICE
CERTIFICATE OF CORRECTION

Page 1 of 1

PATENT NO. : 12,016,762 B2
APPLICATION NO. : 17/959385
DATED : June 25, 2024
INVENTOR(S) : Gabriele Sablone and Massimiliano Rossetti It is certified that error appears in the above-identified patent and that said Letters Patent is hereby corrected as shown below:

On the Title Page

Item (71) should be listed as:
- Fameccanica.Data S.p.A., San Giovanni Teatino (Chieti), ITALY -

Item (72) should be listed as:
- Gabriele SABLONE, San Giovanni Teatino (Chieti), ITALY
Massimiliano ROSSETTI, San Giovanni Teatino (Chieti), ITALY -

Signed and Sealed this
Eleventh Day of March, 2025

Coke Morgan Stewart
*Acting Director of the United States Patent and Trademark Office*